US007262210B2

(12) United States Patent
Kreutter et al.

(10) Patent No.: US 7,262,210 B2
(45) Date of Patent: Aug. 28, 2007

(54) FLUORINATED PYRIDINE N-OXIDE THROMBIN MODULATORS AND PROCESS FOR N-OXIDATION OF NITROGEN CONTAINING HETEROARYLS

(75) Inventors: Kevin Kreutter, Plainsboro, NJ (US); Tianbao Lu, Churchville, PA (US); Yu Kai Lee, Exton, PA (US); Christopher Teleha, Fort Washington, PA (US); Mark Player, Phoenixville, PA (US); Xizhen Zhu, Cranbury, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/385,056

(22) Filed: Mar. 21, 2006

(65) Prior Publication Data

US 2006/0241148 A1  Oct. 26, 2006

Related U.S. Application Data

(60) Provisional application No. 60/673,131, filed on Apr. 20, 2005.

(51) Int. Cl.
*A61K 31/44* (2006.01)
*C07D 213/00* (2006.01)
(52) U.S. Cl. ...................... 514/332; 546/265
(58) Field of Classification Search ............... 546/265; 514/332
See application file for complete search history.

(56) References Cited

U.S. PATENT DOCUMENTS

| | | | |
|---|---|---|---|
| 4,187,379 A | 2/1980 | Butler | |
| 5,028,617 A | 7/1991 | Lindel et al. | |
| 5,481,032 A | 1/1996 | Pfirmann | |
| 5,559,113 A | 9/1996 | Schwartz et al. | |
| 2002/0193398 A1 | 12/2002 | Barrow et al. | |
| 2002/0198199 A1 | 12/2002 | South et al. | |
| 2003/0158218 A1* | 8/2003 | Nantermet et al. | 514/275 |
| 2005/0070715 A1 | 3/2005 | Bhat et al. | |

FOREIGN PATENT DOCUMENTS

| | | |
|---|---|---|
| EP | 0379928 A2 | 1/1990 |
| EP | 0516069 A1 | 5/1992 |
| EP | 0516069 B1 | 5/1992 |
| WO | WO 92/05271 | 4/1992 |
| WO | WO 93/14070 | 7/1993 |
| WO | WO 97/24122 | 7/1997 |
| WO | WO 99/45927 | 9/1999 |
| WO | WO 02/42272 A2 | 5/2002 |
| WO | WO 2004/091613 A2 | 10/2004 |

OTHER PUBLICATIONS

Burgery, et al., Metabolism-Directed Optimization of 3-Aminopyrazinone Acetamide Thrombin Inhibitors. Development of an Orally Bioavailable Series Containing P1 and P3 Pyridines, Amer Chem Soc (2003), 46, pp. 461-473.

Burgery, et al., Pharmacokinetic Optimization of 3-Amino-6-chloropyrazinone Acetamide Thrombin Inhibitors. Implementation of P3 Pyridine N-Oxides to Deliver an Orally Bioavailable Series Containing P1 *N*-Benzylamides, Bioorganic & Med Chem Letters 13 (2003) 1353-1357.

Caron, et al., A practical, efficient, and rapid method for the oxidation of electron deficient pyridines using trifluoroacetic anhydride and hydrogen peroxide-urea complex, Tetrahedron Letters 41 (2000) 2299-2302.

Euler, et al., Influence of physicochemical properties and intestinal region on the absorption of 3-fluoro-2pyrimidylmethyl 3-(2,2-difluoro-2-(2-pyridyl)ethylamino)-6-chloropyrazin-2-one-1-acetamide, a water insoluble thrombin inhibitor, in dogs, International Journal of Pharmaceutics 275 (2004) 19-27.

Murata, et al., A Selective Procedure for 6-Substituted Pterin Derivatives: Synthesis and Substitution of Pterin 6- Triflate, Kluwer Academic Publishers 19-23 (2006).

Nantermet, et al., $P_2$ pyridine N-oxide thrombin inhibitors: a novel peptidomimetic scaffold, Bioorganic & Med Chem Letters (2005) 1-5.

Subramanian, et al., Bioactivation of the 3-Amino-6-Chloropyrazinone Ring in a Thrombin Inhibitor Leads to Novel DiHydro-Imidazole and Imidazolidine Derivatives: Structures and Mechanism Using $^{13}$C-Labels, Mass Spectrometry, and NMR, The Amer Soc for Pharm and Experimental Therapeutics (2003) vol. 31 No. 11, 1437-1447.

* cited by examiner

*Primary Examiner*—Thomas McKenzie
*Assistant Examiner*—Binta Robinson

(57) ABSTRACT

The present invention describes compounds of Formula I

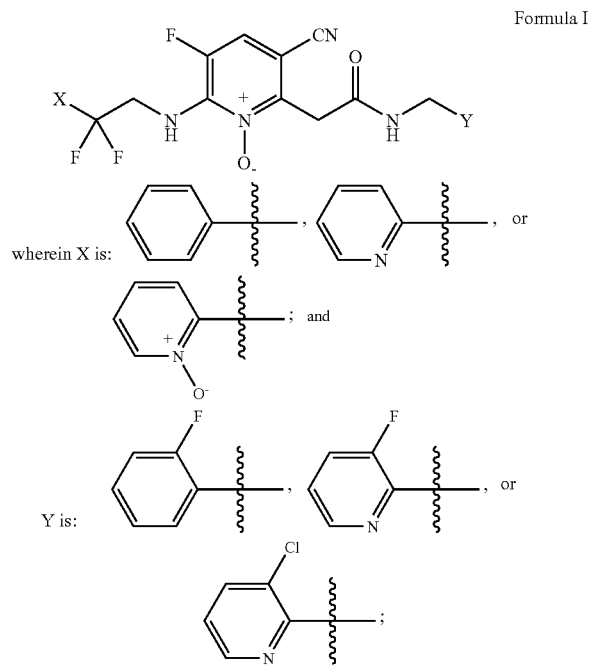

or a pharmaceutically acceptable salt thereof, for the prophylaxis, or treatment of diseases and conditions related to thrombin activity in a mammal. The present invention also relates to a novel method of N-oxidation of nitrogen containing heteroaryls.

8 Claims, No Drawings

FLUORINATED PYRIDINE N-OXIDE THROMBIN MODULATORS AND PROCESS FOR N-OXIDATION OF NITROGEN CONTAINING HETEROARYLS

This application claims priority to provisional application, which is U.S. Ser. No. 60/673,131, filed on Apr. 20, 2005. The complete disclosures of the aforementioned related U.S. patent applications are hereby incorporated herein by reference for all purposes.

FIELD OF THE INVENTION

The present invention relates to novel compounds that function as thrombin inhibitors; the present invention also relates to a novel method of N-oxidation of nitrogen containing heteroaryls.

BACKGROUND OF THE INVENTION

The serine protease thrombin occupies a central role in hemostasis and thrombosis, and as a multifactorial protein, induces a number of effects on platelets, endothelial cells, smooth muscle cells, leukocytes, the heart, and neurons. Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor, and autoamplifies its own production through a feedback mechanism. Thus, inhibitors of thrombin function have therapeutic potential in a host of cardiovascular and non-cardiovascular diseases.

In vivo diagnostic imaging methods for intravascular thrombi have been previously reported. These imaging methods use compounds that are detectably labeled with radioactive or paramagnetic atoms. For example, platelets labeled with the gamma emitter, In-111, can be employed as an imaging agent for detecting thrombi. In addition, the use of the paramagnetic contrasting agent, gadolinium diethylenetriaminepentaacetic acid in magnetic resonance imaging of patients treated by thrombolysis for acute myocardial infarction has been reported.

A need continues to exist for non-peptidic compounds that are potent and selective protease inhibitors, and which possess greater bioavailability and fewer side-effects than currently available protease inhibitors. Accordingly, new protease inhibitors, characterized by potent inhibitory capacity and low mammalian toxicity, are potentially valuable therapeutic agents for a variety of conditions, including treatment of a number of mammalian proteolytic disease states.

The oxidation of pyridines and other N-containing heteroaryls such as pyrimidines, quinolines, pyrazines, benzoxadiazoles, and pyridazinoquinolines to their N-oxides is sometimes employed in drug discovery programs. Numerous methods have been developed to effect this transformation. In many cases, this transformation can be accomplished using a peracid such as, meta-chloroperbenzoic acid, magnesium monoperphthalate, or a peracid formed in situ from, for example, 30% aqueous hydrogen peroxide and trifluoroacetic anhydride or acetic anhydride. Some electron deficient pyridines can be oxidized using catalytic MTO (MeReO$_3$) and 30% H$_2$O$_2$ as the co-oxidant, or trifluoroacetic anhydride and hydrogen peroxide-urea complex (*Tet. Lett.* 41:2299, 2000), or peroxysulfuric acid formed in situ from Oxone® and sulfuric acid (*J. Org. Chem.* 42:1869, 1977). It is not unusual to encounter difficulties in transforming highly electron deficient pyridines to N-oxides using above methods; see, for example, *Tet. Lett.* 41:2299, 2000. The need exists for a practical method for the oxidation of highly electron deficient nitrogen containing heteroaryls to their N-oxides.

SUMMARY OF THE INVENTION

The present invention is directed to the novel compounds of Formula I (below). Also provided are processes for preparing the compounds of Formula I. The novel compounds of the present invention are potent inhibitors of thrombin. Also provided are methods of treating thrombosis in a mammal by administering an effective amount of a compound of Formula I.

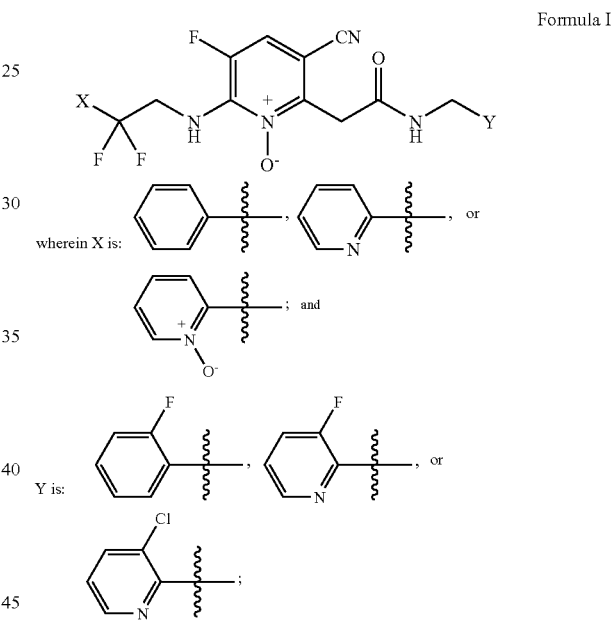

Formula I

The invention also includes a general method of oxidizing nitrogen containing heteroaryls to their corresponding N-oxides. The reagent system can be prepared from relatively safe and commercially available reagents. Moreover, the reaction takes place in neutral to acidic conditions that, for example, are tolerated by the somewhat acid sensitive methyl ester and nitrile groups.

The invention includes a composition for inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

Also provided are methods for treating myocardial infarction; unstable angina; stroke; restenosis; deep vein thrombosis; disseminated intravascular coagulation caused by trauma, or septic hemodialysis; cardiopulmonary bypass surgery; adult respiratory distress syndrome; endotoxic shock; hypercoagulability during chemotherapy; Alzheimer's disease; and fibrin formation in the eye. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents.

The invention also includes a method for reducing the thrombogenicity of a surface in a mammal by attaching to the surface, either covalently or noncovalently, a compound of the invention.

In another aspect, the present invention includes compositions which are useful for in vivo imaging of thrombi in a mammal, comprising a compound of the present invention which is capable of being detected from outside the body. Preferred are compositions comprising a compound of the present invention and a detectable label, such as a radioactive or paramagnetic atom.

In another aspect, the present invention provides diagnostic compositions which are useful for in vivo imaging of thrombi in a mammal, comprising a pharmaceutically acceptable carrier and a diagnostically effective amount of a compound or composition of the present invention.

In another aspect, the present invention includes methods which are useful for in vivo imaging of thrombi in a mammal.

DETAILED DESCRIPTION OF THE INVENTION

The present invention is directed toward compounds of Formula I.

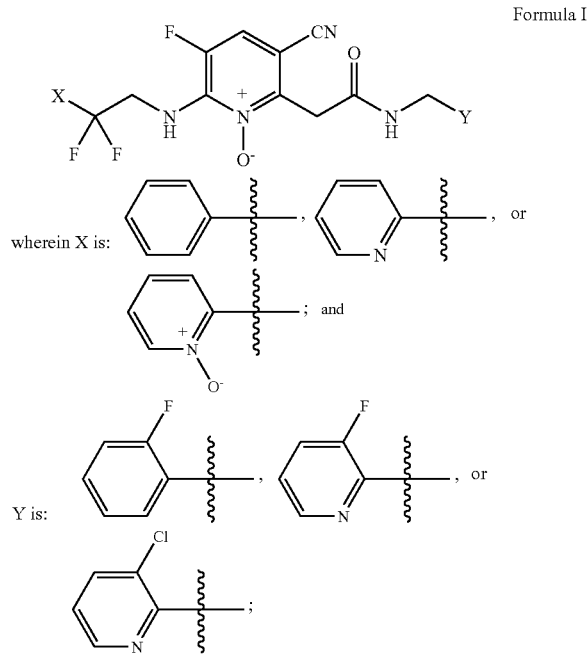

A preferred embodiment of the invention is where X is

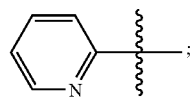

another preferred embodiment of the invention is where Y is

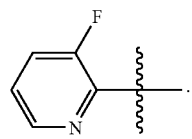

A preferred example of the invention is: 2-[3-Cyano-6-(2,2-difluoro-2-pyridin-2-yl-ethylamino)-5-fluoro-1-oxy-pyridin-2-yl]-N-(3-fluoro-pyridin-2-ylmethyl)-acetamide and pharmaceutically acceptable salts thereof.

A preferred example of the invention is: 2-[3-Cyano-6-(2,2-difluoro-2-pyridin-2-yl-ethylamino)-5-fluoro-1-oxy-pyridin-2-yl]-N-(3-fluoro-pyridin-2-ylmethyl)-acetamide dihydrochloride.

A preferred example of the invention is: 2-[3-Cyano-6-(2,2-difluoro-2-pyridin-2-yl-ethylamino)-5-fluoro-1-oxy-pyridin-2-yl]-N-(3-fluoro-pyridin-2-ylmethyl)-acetamide monohydrobromide.

A preferred example of the invention is: 2-[3-Cyano-6-(2,2-difluoro-2-pyridin-2-yl-ethylamino)-5-fluoro-1-oxy-pyridin-2-yl]-N-(3-fluoro-pyridin-2-ylmethyl)-acetamide sulfonate.

A preferred example of the invention is: 2-[3-Cyano-6-(2,2-difluoro-2-pyridin-2-yl-ethylamino)-5-fluoro-1-oxy-pyridin-2-yl]-N-(3-fluoro-pyridin-2-ylmethyl)-acetamide napthalene-1,5-disulfonate.

The compounds of the present invention may also have polymorphic crystalline forms, with all polymorphic crystalline forms being included in the present invention.

The compounds of Formula I may also be solvated, especially hydrated. Hydration may occur during manufacturing of the compounds or compositions comprising the compounds, or the hydration may occur over time due to the hygroscopic nature of the compound.

In another aspect, the present invention includes compositions which are useful for in vivo imaging of thrombi in a mammal, comprising the compounds of the present invention which is capable of being detected outside the body. Preferred are compositions comprising a compound of the present invention and a detectable label, such as a radioactive or paramagnetic atom.

In another aspect, the present invention provides diagnostic compositions which are used for in vivo imaging of thrombi in a mammal, comprising a pharmaceutically acceptable carrier and a diagnostically effective amount of a compound or composition of the present invention.

In another aspect, the present invention includes methods which are useful for in vivo imaging of thrombi in a mammal.

According to a preferred aspect, useful compounds are those wherein the pyridine substituent, which is adjacent to the difluoromethylene, is substituted with a detectable label, such as a radioactive iodine atom, such as I-125, I-131 or I-123. The detectable label can also be a radioactive or paramagnetic chelate in which a suitable ligand (L) is attached to said pyridine substituent, either directly or via a divalent linking group A". By suitable ligand is meant an organic moiety that is capable of chelating a radioactive or paramagnetic metal ion.

In these compounds, the divalent linking group A" includes groups that are capable of covalently bonding with both the pyridyl and the chelating means. For example, A" may be —C(=S)—, —C(=O)—, —C(=NH)—(CH$_2$)$_6$—C(=NH)—, —C(=O)—(CH$_2$)$_6$—C(=O)—, and the like.

Also, in the compounds represented by Formula I, the chelating ligand, L, includes groups capable of covalently bonding to or noncovalently binding to either a radioactive or paramagnetic atom. The chelating means including those which are customarily used for complexing radioactive or paramagnetic atoms. These include chelating means containing 3 to 12, preferably 3 to 8, methylene phosphonic acid groups, methylene carbohydroxamic acid groups, carboxyethylidene groups, or especially carboxymethylene groups, which are bonded to a nitrogen atom. If only one or two of the acid groups are bonded to a nitrogen atom, then that nitrogen is bonded to another nitrogen atom having such groups by an optionally substituted ethylene group or by up to four separated ethylene units separated by a nitrogen or oxygen or sulfur atom. Preferred as a completing means is diethylenetrimine-N,N,N',N",N"-pentaacetic acid (DTPA). DTPA is well known in the art as a chelating means for the radioactive atoms indium-111 (In-111), technetium-99m (Tc-99m), and the paramagnetic atom gadolinium (Gd). Khaw, et al., *Science* 209:295 (1980); Paik C. H. et al., U.S. Pat. No. 4,652,440 (1987); Gries, H. et al., U.S. Pat. No. 4,957,939 (1990). A preferred chelating ligand, L, is 1-(para-aminobenzyl)-diethylenetriaminepentaacetic acid. Also included as chelating means are compounds which contain sulfhdryl or amine moieties, the total of which in any combination is at least four. These sulfhydryl or amine moieties are separated from each other by at least two atoms which can be either carbon, nitrogen, oxygen, or sulfur. Especially preferred for chelating means, L, is metallothionein which is well known in the art as a chelating means for Tc-99m.

The compounds of Formula I can be labeled with radioactive iodine by using an exchange reaction. Exchange of hot iodine for cold iodine is well known in the art. Alternatively, a radio iodine labeled compounds can be prepared from the corresponding bromo compound via a tributylstannyl intermediate. See, U.S. Pat. No. 5,122,361, herein incorporated by reference.

The present invention also includes compositions which are useful for in vivo imaging of thrombi in a mammal, wherein the compositions are comprised of the compounds of Formula I complexed with a radioactive atom; suitable radioactive atoms include Co-57, Cu-67, Ga-67, Ga-68, Ru-97, Tc-99m, In-111, In-113m, Hg-197, Au-198, and Pb-203. Some radioactive atoms have superior properties for use in radiochemical imaging techniques. In particular, technetium-99m (Tc-99m) is an ideal radioactive atom for imaging because of its nuclear properties. Rhenium-186 and -188 also have gamma emission which allows it to be imaged. Preferred compositions contain the radioactive atom, Tc-99m.

The compounds of Formula I can be labeled by any of the many techniques known in the art to provide a composition of the present invention. For example, the compounds can be labeled through a chelating agent such as diethylene-tri-aminepentaacetic acid (DTPA) or metallothionein, both of which can be covalently attached to the compounds of Formula I.

In general, the compositions of the present invention containing technetium-99m are prepared by forming an aqueous mixture of technetium-99m and a reducing agent and a water-soluble ligand, and then contacting the mixture with a compound of the present invention represented by Formula I. For example, the imaging compounds of this invention are made by reacting technetium-99m (in an oxidized state) with the compounds of the present invention having a chelating means in the presence of a reducing agent to form a stable complex between technetium-99m in a reduced state (IV or V valence state).

One embodiment of the composition of the present invention is prepared by labeling a compound of Formula I having a DTPA chelating means with technetium-99m. This may be accomplished by combining a predetermined amount (as 5 μg to 0.5 mg) of a compound of the present invention with an aqueous solution containing citrate buffer and stannous reducing agent, then adding freshly eluted sodium pertechnetate containing a predetermined level of radioactivity (as 15 mCi). After allowing an incubation of the mixture at room temperature, the reaction mixture is loaded into a shielded syringe through a sterile filter (0.2-0.22 micron), then is dispensed into 0.9% saline for injection, if desired.

Another embodiment of the compositions of the present invention is prepared by labeling a compound of Formula I having a metallothionein chelating means with technetium-99m. This may be accomplished by combining aqueous sodium pertechnetate-99m with aqueous stannous glucoheptonate to form a soluble complex of technetium-99m (in reduced state) with two glucoheptonate molecules, then combining this solution with a compound of Formula I having a metallothionein attached thereto. After incubating the mixture for a period of time and under conditions which allow for an exchange of the technetium-99m from the glucoheptonate complex to the metallothionein of a compound of Formula I, the technetium-labeled composition of the present invention is formed.

Reducing agents for use in the method are physiologically acceptable for reducing technetium-99m from its oxidized state to the IV or V valence state or for reducing rhenium from its oxidized state. Reducing agents which can be used are stannous chloride, stannous fluoride, stannous glucoheptonate, stannous tartarate, and sodium dithionite. The preferred agents are stannous reducing agents, especially stannous chloride or stannous glucoheptonate. The amount of reducing agent is that amount necessary to reduce the technetium-99m to provide for the binding to the chelating means of a compound of Formula I in this radioisotope's reduced state. For example, stannous chloride (SnCl$_2$) is the reducing agent and can be used in range from 1-1,000 μg/mL.

Citric acid complexes with technetium-99m quickly to form a stable technetium-99m-citrate complex. Upon contact with a compound of Formula I, substantially quantitative transfer of technetium-99m from its citrate complex to the chelating means of a compound of Formula I is achieved rapidly and under mild conditions. The amount of citric acid (as sodium citrate) can range from about 0.5 mg/ml up to the amount maximally soluble in the medium. Preferred amounts of citric acid range from 15 to 30 μg/ml.

The amount of compound of Formula I having a chelating means can range from 0.001 to about 3 mg/mL, preferably about 0.017 to about 0.15 mg/mL. Finally, technetium-99m in the form of pertechnetate can be used in amounts of preferably about 1-50 mCi. The amount of mCi per mg of compound of the present invention is preferably about 30-150.

The reaction between a compound of Formula I and the metal ion-transfer ligand complex is preferably carried out in an aqueous solution at a pH at which a compound of Formula I is stable. By "stable", it is meant that the compound remains soluble and retains its inhibitory activity against a-thrombin. Normally, the pH for the reaction will be from about 5 to 9, the preferred pH being above 6-8. The technetium-99m-citrate complex and a compound of Formula I are incubated, preferably at a temperature from about 20° C. to about 60° C., most preferably from about 20° C. to about 37° C., for a sufficient amount of time to allow transfer of the metal ion from the citrate complex to the chelating means of the compound of Formula I. Generally, less than one hour is sufficient to complete the transfer reaction under these conditions.

Alternative compositions of the present invention include an In-111 labeled compound of the present invention.

The present invention also includes compositions of the compounds of the present invention which are useful for in vivo imaging of thrombi in a mammal, comprised of the compounds represented by Formula I complexed to a paramagnetic atom.

Preferred paramagnetic atoms are divalent or trivalent ions of elements with an atomic number of 21 to 29, 42, 44 and 58 to 70. Suitable ions include chromium(III), manganese(II), iron(III), iron(II), cobalt(II), nickel(II), copper(II), praseodymium(III), neodymium(III), samarium(III) and ytterbium(III). Because of their very strong magnetic moments, gadolinium(III), terbium(III), dysoprosium(III), holmium(III), and erbium(III) are preferred. Especially preferred for the paramagnetic atom is gadolinium(III).

The compositions of the present invention may be prepared by combining a compound of Formula I with a paramagnetic atom. For example, the metal oxide or a metal salt (for example, nitrate, chloride or sulfate) of a suitable paramagnetic atom is dissolved or suspended in a medium comprised of water and an alcohol, such as methyl, ethyl or isopropyl alcohol. This mixture is added to a solution of an equimolar amount of a compound of Formula I in a similar aqueous medium and stirred. The reaction mixture may be heated moderately until the reaction is completed. Insoluble compositions formed may be isolated by filtering, while soluble compositions may be isolated by evaporation of the solvent. If acid groups on the chelating means are still present in the composition of the present invention, inorganic or organic bases, and even amino acids, may be added to convert the acidic complex into a neutral complex to facilitate isolation or purification of homogenous composition. Organic bases or basic amino acids may be used as neutralizing agents, as well as inorganic bases such as hydroxides, carbonates or bicarbonates of sodium, potassium or lithium.

The present invention also includes diagnostic compositions which are useful for in vivo imaging of thrombi in a mammal, comprising a pharmaceutically acceptable carrier and a diagnostically effective amount of a composition derived from a compound of Formula I.

The "diagnostically effective amount" of the composition required as a dose will depend on the route of administration, the type of mammal being treated, and the physical characteristics of the specific mammal under consideration. These factors and their relationship to determining this dose are well known to skilled practitioners in the medial diagnostic arts. Also, the diagnostically effective amount and method of administration can be tailored to achieve optimal efficacy but will depend on such factors as weight, diet, concurrent medication and other factors which those skilled in the medical arts will recognize. The dose for imaging should be sufficient for detecting the presence of the imaging agent at the site of a thrombus in question. Typically, radiologic imaging will require that the dose provided by the pharmaceutical composition position of the present invention be about 5 to 20 µCi, preferably about 10 µCi. Magnetic resonance imaging will require that the dose provided be about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

"Pharmaceutically acceptable carriers" for in vivo use are well known in the pharmaceutical art, and are described, for example, in *Remington's Pharmaceutical Sciences,* Mack Publishing Co. (A. R. Gennaro edit. 1985). The pharmaceutical compositions of the present invention may be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

The present invention also encompasses diagnostic compositions prepared for storage or administration. These would additionally contain preservatives, stabilizers and dyes. For example, sodium benzoate, sorbic acid and esters of para-hydroxybenzoic acid may be added as preservatives. Idem at 1449. In addition, antioxidants and suspending agents may be used.

The in vivo imaging methods of the present invention also offer several advantages over previous imaging techniques for the detection or monitoring of the presence, size, regression or increase of a thrombus. In particular, the present invention provides compounds, compositions and diagnostic compositions that bind tightly to the thrombin associated with a thrombus and thereby reduce "background" due to circulating radioactivity or paramagnetism arising from unbound imaging agent. Furthermore, in vivo imaging by intracoronary injection of the compounds, compositions or diagnostic compositions of the present invention, is expected to be almost instantaneous since these imaging agents would saturate the thrombin bound to the thrombus immediately.

Accordingly, the present invention also includes methods for in vivo imaging of a thrombus in a mammal, comprising the steps of: (1) administering to a mammal a diagnostically acceptable amount of a compound, composition, or diagnostic composition of the present invention and (2) detecting a thrombus in a blood vessel.

The term "in vivo imaging" as used herein relates to methods of the detection of a thrombus in a mammal, as well as the monitoring of the size, location and number of thrombi in a mammal, as well as dissolution or growth of the thrombus.

In employing the compounds, compositions or diagnostic compositions in vivo by this method, "administering" is accomplished parenterally, in either a systemic or local targeted manner. Systemic administration is accomplished by injecting the compounds, compositions by diagnostic compositions of the present invention into a convenient and accessible vein or artery. This includes but is not limited to administration by the antecubital vein. Local targeted administration is accomplished by injecting the compounds, compositions or diagnostic compositions of the present invention proximal in flow to a vein or artery suspected to contain thrombi distal to the injection site. This includes but is not limited to direct injection into the coronary arterial vasculature to image coronary thrombi, into the carotid artery to image thrombi in the cerebral vasculature, or into a pedal vein to image deep vein thrombosis of the leg.

Also, the manner of delivery of a composition of the present invention to the site of a thrombus is considered within the scope of the term "administering". For example, a compound represented by Formula I having a chelating means attached thereto may be injected into the mammal, followed at a later time by the radioactive atom thereby forming in vivo at the site of the thrombus the composition comprising a compound of Formula I complexed to a radioactive atom. Alternatively, a composition comprising a compound of Formula I complexed to a radioactive atom may be injected into the mammal.

The "diagnostically effective amount" of the compounds, compositions or diagnostic compositions used in the methods of the present invention will, as previously mentioned, depend on the route of administration, the type of mammal being treated, and the physical characteristics of the specific mammal under treatment. These factors and their relationship to determining this dose are well known to skilled practitioners in the medical diagnostic arts. The dose for in vivo imaging should be sufficient for detecting the presence of the imaging agent at the site of a thrombus in question. Typically, radiologic imaging will require that the dose provided by the diagnostic composition of the present invention be about 5 to 20 μCi, preferably about 10 μCi. Magnetic resonance imaging will require that the dose provided by the diagnostic composition be about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

The detecting of a thrombus by imaging is made possible by the presence of radioactive or paramagnetic atoms localized at such thrombus.

The radioactive atoms associated with the compositions and diagnostic compositions of the present invention are preferably imaged using a radiation detection means capable of detecting gamma radiation, such as a gamma camera or the like. Typically, radiation imaging cameras employ a conversion medium (wherein the high energy gamma ray is absorbed, displacing an electron which emits a photon upon its return to its ground state), photoelectric detectors arranged in a spatial detection chamber (to determine the position of the emitted photons), and circuitry to analyze the photons detected in the chamber and produce an image.

The paramagnetic atoms associated with the compositions and diagnostic compositions of the present invention are detected in magnetic resonance imaging (MRI) systems. In such systems, a strong magnetic field is used to align the nuclear spin vectors of the atoms in a patient's body. The field is disturbed by the presence of paramagnetic atoms localized at a thrombus and an image of the patient is read as the nuclei return to their equilibrium alignments.

Definitions

The term "about" as employed herein is intended to mean +/−15% when modifying a quantity of reagent used; for example "about 1 mmol" refers to a range from 0.85 mmol to 1.15 mmol. The term "about" as employed herein is intended to mean +/−5° C. when referring to a temperature; for example, "about 40° C." refers to a temperature range from 35° C. to 45° C.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl. Preferably, alkyl is 1 to 6 carbon atoms.

The term "alkenyl" is used herein to mean a straight or branched chain radical of 2-20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2-20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage, is preferably not directly attached to a nitrogen, oxygen or sulfur moiety.

The term "electron withdrawing group" refers to a substituent which brings electron density towards itself and away from other areas. Examples of electron withdrawing groups are: phenyl, heteroaryl, halogen, —$NO_2$, —CN, sulfone, sulfoxide, ester, sulfonamide, carboxamide, alkoxy, alkoxyether, alkenyl, alkynyl, —OH, —C(O)alkyl, —$CO_2H$, —Ophenyl, —Oheteroaryl, and —$CF_3$.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_8$ alkyl, or together with the nitrogen to which they are bound, form a saturated or unsaturated 5-, 6-, or 7-membered ring.

The term "triflate" refers to the anion trifluoromethane sulfonate, $CF_3SO_3^-$, abbreviated OTf⁻. The adjectival form of "triflate" is "triflic". For example, triflic anhydride refers to trifluoromethane sulfonate anhydride, $(CF_3SO_2)_2O$, abbreviated $Tf_2O$.

Pharmaceutically Acceptable Salts

The pharmaceutically acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, trifluoroacetate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth, including salts with a guanidinyl moiety. Also, the basic nitrogen-containing groups may be quaternized with such agents as lower alkyl halides, such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; aralkyl halides like benzyl and phenethyl bromides and others. Preferred acids for forming acid addition salts include HCl, HBr, sulfuric acid and naphthalene-1,5-sulfuric acid.

Applications

For their end-use application, the present invention may be employed for a number of therapeutic purposes. The present invention inhibits thrombin. Therefore, these compounds are useful for the treatment or prophylaxis of states characterized by abnormal venous or arterial thrombosis involving either thrombin production or action. These states include, but are not limited to, deep vein thrombosis; pulmonary embolism; arterial thrombosis; systemic embolism usually from the atrium during arterial fibrillation or from the left ventricule after transmural myocardial infacrtion; unstable angina; restenosis; adult respiratory distress syndrome; endotoxic shock; hypercoagulability during or after chemotherapy or radiotherapy; disseminated intravascular coagulopathy which occurs during septic shock, viral infections and cancer; myocardial infarction; stroke; coronary artery bypass; fibrin formation in the eye; orthopedic surgery such as hip replacement; and thrombus formation resulting from either thrombolytic therapy or percutaneous transluminal coronary angioplasty (PCTA). A preferred use of the invention is for the prophylaxis or treatment of deep vein thrombosis.

Compounds of the present invention are expected to have utility in the treatment and prophylaxis of disseminated intravascular coagulation caused by any mechanism including bacteria, multiple trauma, and intoxication.

Compounds of the present invention are expected to be useful in situations where there are elevated thrombin levels without signs of hypercoagulability, such as in Alzheimer's disease and pancreatitis.

Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, and blood lines. The compounds of the present invention may also be used as an anticoagulant in extracorporeal blood circuits.

Stents have been shown to reduce restenosis, but are thrombogenic. A strategy for reducing the thrombogenicity of stents is to coat, embed, adsorb or covalently attach a thrombin-inhibiting agent to the stent surface. The compounds of the present invention can be employed for this purpose. Compounds of the invention can be attached to, or embedded within soluble and/or biodegradable polymers as and thereafter coated onto stent materials. Such polymers can include polyvinylpyrrolidone, polyhydroxy-propyl-methacrylamide-phenol, polyhydroxyethyl-aspartamide-phenol, or polyethyleneoxide-polylysine substituted with palmitoyl residues, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent No. 2,164,684 and PCT Published Applications Nos. WO 96/11668, WO 96/32143 and WO 96/38136.

By virtue of the effects of thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stent placement.

The compounds of the present invention may be useful in treating neurodegenerative diseases, such as Alzheimer's disease and Parkinson's disease.

The compounds of the present invention may be administered in an effective amount within the dosage range of about 0.1 to about 500 mg/kg, preferably between 0.1 to 10 mg/kg body weight, on a regimen in single or 2-4 divided daily doses.

The compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

The compounds of the present invention may also be coupled with soluble polymers as targetable drug carriers. Such polymers can include polyvinylpyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

For compositions of the present invention suitable for administration to a human, the term "excipient" is meant to include, but not be limited by, those excipients described in the *Handbook of Pharmaceutical Excipients,* American Pharmaceutical Association, $2^{nd}$ Ed. (1994), which is herein incorporated by reference in its entirety. Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxy-propylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered and obvious to those skilled in the art are within the spirit and scope of the invention.

General Synthetic Methods

Compounds of the present invention may be synthesized according to Scheme I.

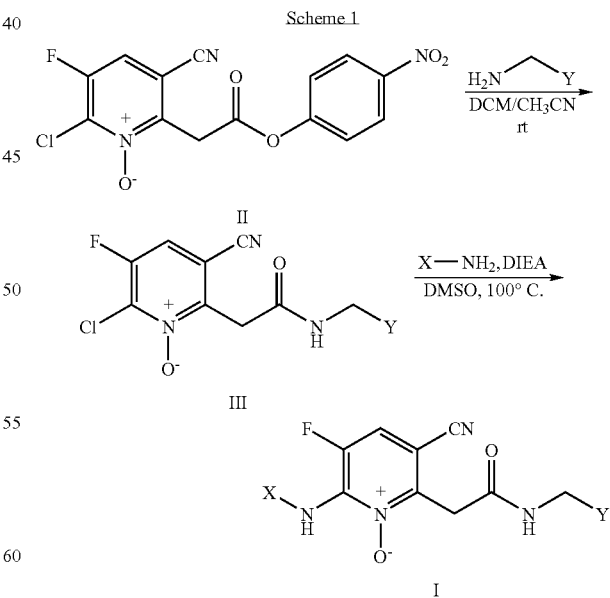

A solution of $H_2N$—$CH_2$—Y in solvents such as DCM or $CH_3CN$ is added to a mixture of (6-chloro-3-cyano-5-fluoro-1-oxy-pyridin-2-yl)-acetic acid 4-nitro-phenyl ester, as prepared in Example 1i, in a solvent such as $CHCl_3$ at a temperature from −40° C. to 150° C., preferably room temperature, under air to provide compound III. Compounds of formula H$_2$N—CH$_2$—Y are either commercially available or may be synthesized according to known methods; see: *Org. Process Res. Dev.* Vol 8, p. 192, 2004, and *J. Med. Chem.* Vol 46, p. 461, 2003. A mixture of compound III, X-NH$_2$, a base such as diisopropylethylamine (DIEA), and a solvent such as DMSO is then stirred under air at a temperature from rt to 150° C., preferably 100° C. to provide compound I. Compounds of formula X-NH$_2$ can be made by known methods; see *Org. Process Res. Dev.* Vol 8, p.192, 2004, *J. Org. Chem.* Vol 68, p.8838, 2003, WO 9911267, WO 2004091613, *J. Med. Chem.* 46:461, 2003, and *Chem. Pharm. Bull.* 48:982, 2000.

This application also provides a practical method to prepare not only the novel compounds of the invention, but also a method of wide general applicability for the oxidation of highly electron deficient pyridines and other N-containing heteroaryl compounds to their N-oxides. Preferred N-containing heteroaryls are pyridines, pyrimidines, pyrazines, and quinolines. The reaction takes place in neutral to acidic conditions that are tolerated by certain acid sensitive functional groups. The reaction proceeds in CH$_3$CN or a mixture of CH$_3$CN and DCM (dichloromethane). The reaction is also applicable to electron deficient pyrimidines and electron deficient quinolines. General reaction conditions are shown in Scheme 2.

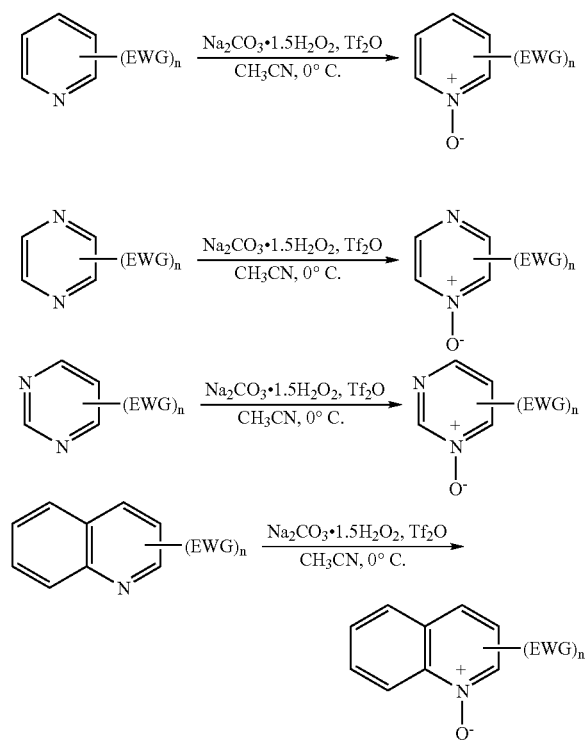

wherein EWG is an electron withdrawing group, preferably halogen, —CF$_3$, ester, or —CN; and
n is 1,2, 3,4, or 5.

Those skilled in the art will recognize that alkyl groups may be present on the heteroaryl in addition to the electron withdrawing group(s). A preferred example is shown in Scheme 3, and a particularly preferred example is one wherein EWG is —CO$_2$alkyl.

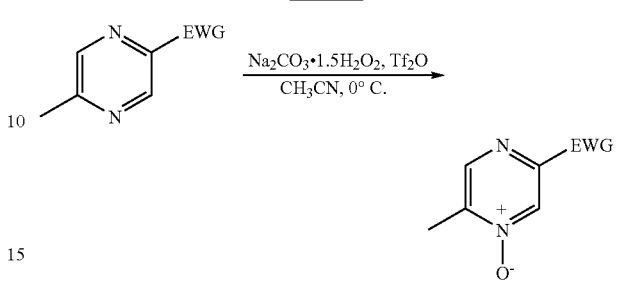

The most important aspects of the reaction are the combination of sodium percarbonate and triflic anhydride. Those skilled in the art will recognize that although the reactions were stopped after either 3.5 hrs or 16 hrs, that the reaction may be successfully run using any time course from about 30 minutes to a week. Checking the reaction by TLC for loss of starting material is the most reliable determination of reaction endpoint. It will also be recognized that temperatures outside the range of 0° C. to room temperature may be used. We anticipate that the reaction can be successfully run in the temperature range of −50° C. to 40° C. Those skilled in the art will also recognize that solvents other than acetonitrile, especially mixtures of solvents such as acetonitrile and methylene chloride can be used (Note: We don't recommend using an ether solvent in the presence of a strong oxidant for safety reasons.) Finally it will be recognized that the steps of quenching the reaction (pouring of the reaction into a mixture of crushed ice and sodium bicarbonate), extracting with methylene chloride, destruction of excess hydrogen peroxide with sodium metabisulfite, and isolating the product using an ISOLUTE® silica cartridge are not critical aspects of the invention, and anyone skilled in the art will be capable of quenching this reaction and isolating the product by alternative methods.

General Procedure: To an oven-dried 4-dram vial is added the pyridine (1.0 mmol), sodium percarbonate (157 mg, 1.0 eq.) and anhydrous CH$_3$CN (5.0 mL). To the suspension, cooled in an ice water bath, is dropwise added triflic anhydride (339 μL, 2.0 eq.). Bubbles form during addition of triflic anhydride. The mixture continues stirring for 3.5 hr at 0° C. Most solid sodium percarbonate disappears after 3 hr. The reaction may be monitored using TLC (or NMR spectrum) of a worked-up aliquot to monitor consumption of starting material, and the reaction may be quenched when the TLC or NMR spectrum indicates that no further reaction is occurring. The reaction mixture is then poured onto a mixture of crushed ice (10 g) and saturated sodium bicarbonate (40 mL). After stirring for 30 min, the mixture is extracted with DCM (3×20 mL). The combined DCM solution is washed with brine (20 mL) and dried over sodium sulfate. The aqueous solution is treated with 10% Na$_2$S$_2$O$_5$ solution. After concentration, the DCM solution is loaded onto a 20 g ISOLUTE® silica cartridge and eluted with Hexane/EtOAc. Table 1 shows representative oxidations of electron deficient pyridines.

TABLE 1

Oxidation of pyridines with Tf$_2$O/Na$_2$CO$_3$-1.5 H$_2$O$_2$ at 0 °C. to RT

| Entry | Product | Solvent | Time (hr) | Yield (%) |
|---|---|---|---|---|
| 1 | 2,6-dichloropyridine N-oxide | CH$_3$CN | 3.5 | 67 |
| 2 | 2,4-dichloropyridine N-oxide | CH$_3$CN | 3.5 | 65 |
| 3 | 2-chloro-3-cyanopyridine N-oxide | CH$_3$CN | 3.5 | 70 |
| 4 | 2-chloro-5-trifluoromethylpyridine N-oxide | CH$_3$CN | 3.5 | 41 |
| 5 | 3,4,5-trichloropyridine N-oxide | CH$_3$CN | 3.5 | 11 |
| 6 | methyl 2,6-dichloroisonicotinate N-oxide | CH$_3$CN | overnight | 79* |
| 7 | 2,3,5,6-tetrachloropyridine N-oxide | CH$_3$CN | overnight | 46* |

TABLE 1-continued

Oxidation of pyridines with Tf$_2$O/Na$_2$CO$_3$-1.5 H$_2$O$_2$ at 0 °C. to RT

| Entry | Product | Solvent | Time (hr) | Yield (%) |
|---|---|---|---|---|
| 8 | 5-F, 2,6-diCl, 3-CO$_2$Me pyridine N-oxide | CH$_3$CN | overnight | 45* |
| 9 | 4-CO$_2$Et, 3-CN, 2-Cl, 6-Me pyridine N-oxide | CH$_3$CN | overnight | 66* |
| 10 | 4-CF$_3$, 3-CN, 2,6-diCl pyridine N-oxide | CH$_3$CN | overnight | 7* |
| 11 | pentachloropyridine N-oxide | CH$_3$CN/CH$_2$Cl$_2$ | overnight | 25* |
| 12 | 4,5,7-triCl, 2-CF$_3$ quinoline N-oxide | CH$_3$CN | 3.5 | 42 |
| 13 | 2,4,6-trichloropyrimidine N-oxide | CH$_3$CN | 3.5 | 14 |

*Overnight reactions were allowed to warm to room temperature over 2 to 3 hours.

Alternatively, a preferred oxidation of an electron deficient pyridine, pyrimidine, quinoline, or pyridazine may be accomplished using urea hydrogen peroxide in place of sodium percarbonste. Preferred reaction conditions are shown in Scheme 4.

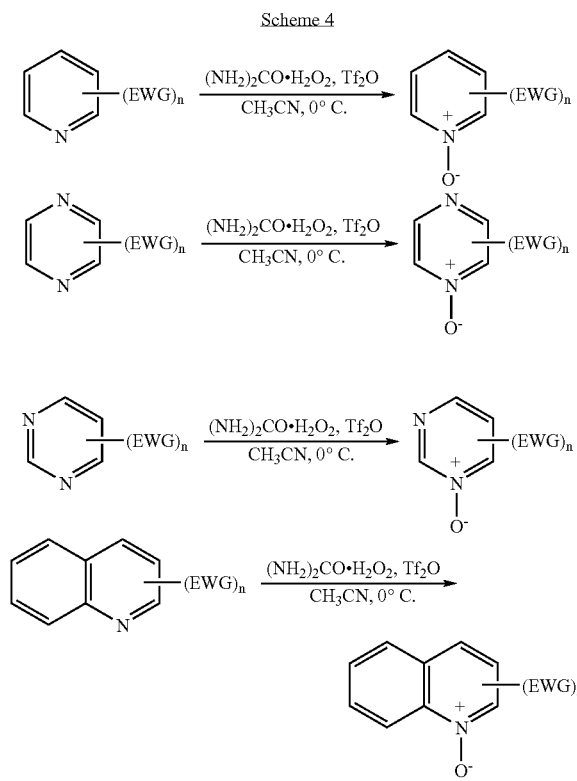

wherein EWG is an electron withdrawing group, preferably halogen, —CF$_3$, ester, or —CN; and n is 1, 2, 3, 4, or 5.

The most important aspects of the reaction are the combination of urea hydrogen peroxide and triflic anhydride.

EXAMPLE 1

2-[3-Cyano-6-(2,2-difluoro-2-pyridin-2-yl-ethylamino)-5-fluoro-1-oxy-pyridin-2-yl]-N-(3-fluoro-pyridin-2-ylmethyl)-acetamide dihydrochloride

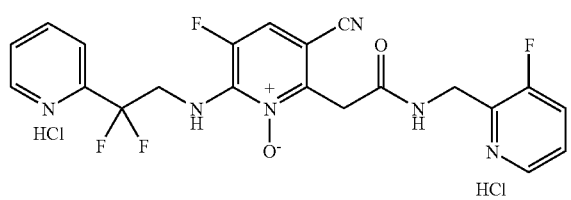

a. 2,5,6-Trifluoro-nicotinonitrile

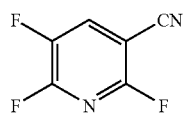

2,6-Dichloro-5-fluoro-nicotinonitrile (25.67 g, 134 mmol) and spray-dried KF (23.6 g, 406 mmol) (Aldrich), both of which had been freshly powdered under air to remove clumps, were shaken together to ensure complete mixing before adding dry DMSO (30 mL). The mixture was efficiently stirred at rt under argon for 1-2 min, and then placed in a 100° C. oil bath and stirred for 5 min. The temperature was then raised to 130° C. over the course of 10 min, and the mixture was stirred at this temperature for 40 min. The NMR spectrum of reaction aliquots demonstrated 86% conversion after 10 min at 130° C., and >95% conversion after 40 min. The thick purple mixture was then allowed to cool to rt, shaken with DCM (30 mL) on an ice bath, and then loaded directly onto a flash silica column (1.0 kg silica gel; 120 mm×6") pre-equilibrated with DCM. DCM elution (140 mL fractions; fractions 10-19 combined) afforded 20.65 g of a clear light amber oil. A NMR spectrum demonstrated a 1:0.58 mol ratio of title compound:DMSO (16.0 g title compound; 76%). $^1$H-NMR (300 MHz, CDCl$_3$) δ 7.99 (m, 1H). LC/MS (ESI): calcd mass 158.0, found 159.5 (MH)$^+$.

b. 6-tert-Butoxy-2,5-difluoro-nicotinonitrile

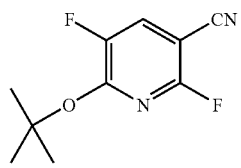

A solution of 1.04 M KOtBu in t-BuOH (110 mL, 114 mmol) pre-mixed with THF (20 mL) was added dropwise over 15 min to a stirred 0° C. solution of 2,5,6-trifluoro-nicotinonitrile (16.0 g, 101 mmol) contaminated with an additional 4.6 g DMSO, as prepared in the preceding step, in t-BuOH (80 mL) and THF (15 mL; to prevent freezing). The resulting homogeneous reddish-amber solution was stirred for an additional 5 min at 0° C., the ice bath was then removed, and the solution stirred for an additional 20 min at rt. The reaction was then quenched with 5 M NH$_4$Cl (100 mL) and extracted with ether (2×100 mL). The combined organic layers were washed with water (1×100 mL), 1 M NaCl (1×150 mL), and 4 M NaCl (1×100 mL), and the clear purple organic layer was dried (Na$_2$SO$_4$), concentrated under reduced pressure, taken up in ether (50 mL), and filtered through a pad of diatomaceous earth. The filter cake was washed with ether (3×50 mL), and the combined filtrates were concentrated under reduced pressure at 50-60° C. to afford 20.89 g of a clear purple oil. NMR indicated an 89:11 mol ratio of the title compound and 2,6-di-tert-butoxy-5-fluoro-nicotinonitrile (18.22 g title compound; 85%). $^1$H-NMR (300 MHz, CDCl$_3$) δ 7.60 (dd, 1H), 1.67 (s, 9H).

c. Malonic acid tert-butyl ester methyl ester, sodium salt

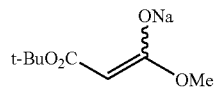

A room temperature mixture of NaH (1.50 g, 59.4 mmol) in ether (50 mL) was placed in a −78° C. bath and was then immediately treated with five approx. 2 mL portions of malonic acid tert-butyl ester methyl ester (10.33 g, 59.4 mmol) under air with intermittent swirling. No bubbles or exotherm occurred. Immediately following completion of addition of the malonate, the loosely capped flask was swirled in a 0° C. bath for 1-2 min (no bubbles), then cautiously at rt for 10 min with intermittent heat gun warming. After gentle bubbling commenced, the reaction was allowed to sit at rt for 1 h with occasional swirling, at which point a thick paste resulted. Volatiles were then removed by rotary evaporation at 40° C., followed by high vacuum at 40° C., to afford the title compound as an easily-handled essentially non-hygroscopic white powder (11.37 g, 98%).

d. 2-(6-tert-Butoxy-3-cyano-5-fluoro-pyridin-2-yl)-malonic acid tert-butyl ester methyl ester

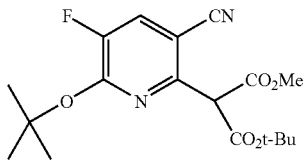

A thick mixture of 6-tert-butoxy-2,5-difluoro-nicotinonitrile (18.22 g, 85.9 mmol), as prepared in Example 1b, malonic acid tert-butyl ester methyl ester sodium salt (34.49 g, 176 mmol), as prepared in the previous step, and dioxane (110 mL) was stirred under argon at 95° C. (oil bath) for 14 h. The resulting homogeneous dark amber solution was allowed to cool to rt, diluted with ether (150 mL), and washed with a solution of 1.0 M $NaH_2PO_4$ (200 mL) containing 2.0 M citric acid (40 mL). The aqueous layer was back-extracted with ether (1×100 mL), the organic layers were combined, washed with 4 M NaCl (1×100 mL), dried ($Na_2SO_4$), and concentrated under reduced pressure. Malonic acid tert-butyl ester methyl ester was largely removed from the residue by high vacuum at 95° C. for 1 h to afford the title compound as a clear, dark brown viscous oil (32.37 g, approx. 100% crude yield). $^1$H-NMR (300 MHz, $CDCl_3$) δ 7.48 (d, 1H), 5.06 (s, 1H), 3.80 (s, 3H), 1.62 (s, 9H), 1.47 (s, 9H).

e. (3-Cyano-5-fluoro-6-hydroxy-pyridin-2-yl)-acetic acid methyl ester

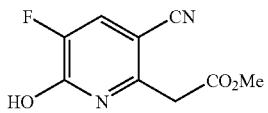

Anisole (6 mL, 55 mmol) and TFA (58 mL, 750 mmol) was added to 2-(6-tert-butoxy-3-cyano-5-fluoro-pyridin-2-yl)-malonic acid tert-butyl ester methyl ester (31.87 g, 87 mmol), as prepared in the previous step, and the homogeneous solution was stirred at 40° C. for 1.5 h. The reaction was then concentrated under rotary evaporation at 40° C., TFA was again added (130 mL, 1.74 mol), and the reaction stirred at rt overnight. The reaction was again concentrated under rotary evaporation at ≦40° C. and the resulting thick oil was dissolved in $CHCl_3$ (100 mL). Next, 2.0 M $K_2CO_3$ (100 mL) was added with stirring in 5-10 mL portions over 5-10 min at 0° C. until the aqueous layer was pH 9. 2.0 M citric acid (30 mL) was added portionwise with stirring at 0° C. to pH 4, and $CHCl_3$ (100 mL) and water (100 mL) was added. The aqueous layer was extracted with $CHCl_3$ (2×100 mL), the organic layers were combined, dried ($Na_2SO_4$), and concentrated to afford a viscous, dark oil (16.6 g). Silica flash chromatography of the residue (9:1→7:3 DCM/acetone) provided the title compound as a yellow solid (9.10 g, 51%). $^1$H-NMR (300 MHz, $CDCl_3$) δ 12.73 (br s, 1H), 7.30 (d, 1H), 3.92 (s, 2H), 3.82 (s, 3H).

f. (6-Chloro-3-cyano-5-fluoro-pyridin-2-yl)-acetic acid methyl ester

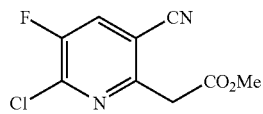

A mixture of (3-cyano-5-fluoro-6-hydroxy-pyridin-2-yl)-acetic acid methyl ester (9.10 g, 43.3 mmol), as prepared in the previous step, and $POCl_3$ (40 mL, 433 mmol) was stirred at 95° C. for 7 h. The homogeneous brown solution was then concentrated under reduced pressure, and the residue was put on an ice bath, diluted with ether (200 mL), and then shaken with ice water (100 mL). The aqueous layer was extracted with ether (1×100 mL), and the organic layers were combined, dried ($Na_2SO_4$), and concentrated under reduced pressure at 40° C. to afford the title compound as a clear dark amber oil (9.45 g, 96%). $^1$H-NMR (300 MHz, $CDCl_3$) δ 7.75 (d, 1H), 4.06 (s, 2H), 3.77 (s, 3H).

g. (6-Chloro-3-cyano-5-fluoro-pyridin-2-yl)-acetic acid

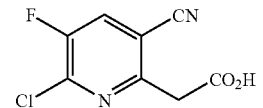

A mixture of (6-chloro-3-cyano-5-fluoro-pyridin-2-yl)-acetic acid methyl ester (9.36 g, 40.9 mmol), as prepared in the previous step, 4.0 M HCl (aq) (256 mL) and dioxane (51 mL) was vigorously stirred at 65° C. for 2 h. The homogeneous amber solution was then allowed to cool to rt, extracted with DCM (3×100 mL), dried (Na$_2$SO$_4$) and concentrated under reduced pressure at 45° C. to provide the title compound as a clear, dark amber oil (7.40 g, 84%). $^1$H-NMR (300 MHz, CDCl$_3$) δ 7.75 (d, 1H), 4.11 (s, 2H).

h. (6-Chloro-3-cyano-5-fluoro-pyridin-2-yl)-acetic acid 4-nitro-phenyl ester

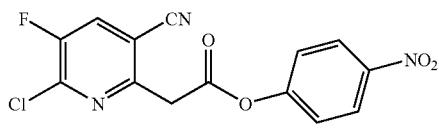

A homogeneous brown solution of (6-chloro-3-cyano-5-fluoro-pyridin-2-yl)-acetic acid (2.37 g, 11.0 mmol), as prepared in the previous step, 4-nitrophenol (1.84 g, 13.2 mmol), and DCM (11 mL) was stirred under argon at 0° C. while 1,3-diisopropylcarbodiimide (DIC) (1.90 mL, 12.1 mmol) was added dropwise with stirring over 3 min. The ice bath was immediately removed following completion of the DIC addition, and the brown mixture with yellowish precipitate was stirred at rt for 1 h 40 min. The crude reaction was then directly loaded onto a flash silica column and eluted with 96:4 toluene/CH$_3$CN to afford the title compound as a translucent pale yellow oil (3.11 g, 84%). $^1$H-NMR (300 MHz, CDCl$_3$) δ 8.29 (m, 2H), 7.80 (d, 1H), 7.35 (m, 2H), 4.35 (d, 0.7 Hz, 2H).

i. (6-Chloro-3-cyano-5-fluoro-1-oxy-pyridin-2-yl)-acetic acid 4-nitro-phenyl ester

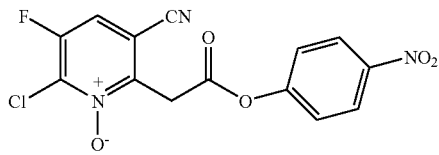

Procedure A

[CAUTION: Although the reaction described below proceeded without incident, it was performed behind a large plexiglas shield.] Solid sodium percarbonate (4.54 g, (containing ~25% wt % (~43 mmol) H$_2$O$_2$) from Aldrich) was added in one portion under air with stirring to a 0° C. pale yellow solution of (6-chloro-3-cyano-5-fluoro-pyridin-2-yl)-acetic acid 4-nitro-phenyl ester (4.85 g, 14.5 mmol), as prepared in the previous step, in CH$_3$CN (110 mL). Triflic anhydride (7.58 g, 26.9 mmol) was then added dropwise with stirring at 0° C. over 11 min immediately following sodium percarbonate addition, and the resulting translucent yellow solution was stirred at 0° C. for 3 h. The reaction was then diluted with ice cold DCM (150 mL) and quenched with ice cold 1 M NaHCO$_3$ (150 mL), and the bilayer was stirred at 0° C. for 7 min. The organic layer was then collected; the aqueous layer was extracted with DCM (2×100 mL), and the combined organic layers were dried (2×Na$_2$SO$_4$), filtered, and concentrated under reduced pressure at rt to provide 4.89 g of the crude title compound (NMR indicates 68 mol % title compound, 25 mol % starting material, and 7 mol % nitrophenol). This material was triturated by stirring with dry ether at rt for 5 min (1×50 mL; 1×25 mL). NMR revealed 84 mol % title compound, 16 mol % starting material, and complete removal of nitrophenol. Four more 20 min triturations by stirring at rt (1×50 mL ether, 1×55 mL 10:1 ether/DCM, 1×50 mL 1:1 ether/DCM, and 1×50 mL DCM), with removal of the clear supernatant after each trituration, afforded the title compound as an off-white solid (2.96 g, 58%). NMR revealed 96 mol % title compound and 4 mol % starting material. $^1$H-NMR (300 MHz, CDCl$_3$) δ 8.29 (m, 2H), 7.46 (d, 1H), 7.36 (m, 2H), 4.37 (d, 0.7 Hz, 2H).

Procedure B (6-Chloro-3-cyano-5-fluoro-pyridin-2-yl)-acetic acid 4-nitro-phenyl ester (35.90 g, 106.95 mmol) was dissolved in acetonitrile (179.50 mL) and cooled to 0° C. using an ice/water bath. Urea hydrogen peroxide (23.14 g, 245.98 mmol) was added to the mixture and stirred for 5 min. Trifluoromethanesulfonic anhydride (66.38 g, 235.28 mmol) was then added dropwise to the reaction mixture at 0° C. over 2.25 h while maintaining the temperature below 3.5° C. After the addition, the mixture was continued to stirr at same temperature for 2 h. Additional Urea hydrogen peroxide (2.3 g, 24.4 mmol), trifluoromethanesulfonic anhydride (4 mL, 23.8 mmol) were added to the mixture and the mixture was then stirred at 0° C. for 30 min. Another aliquot of urea hydrogen peroxide (2.3 g, 24.4 mmol) and trifluoromethanesulfonic anhydride (4 mL, 23.8 mmol) were added to the mixture. The mixture was stirred at 0° C. for 15 min and HPLC indicated the reaction was 96% complete. Sodium bisulfite solution (5%, 1000 mL) was added carefully to the mixture while maintaining the temperature below 10° C. The mixture was allowed to stir at 0° C. in an ice/water bath for 5 min and then stored in a refrigerator overnight. The slurry was filtered and washed with water (2×100 mL and 50 mL). The solid was dried under vacuum at 60° C. for 6 h to yield a brown solid (31.7 g, 84%). $^1$H-NMR (400 MHz, d3-acetonitrile): 8.32 (m, 2H), 7.75 (m, 1H), 7.37 (m, 2H), 4.32 (s, 2H). $^{19}$F-NMR (376 MHz, d3-acetonitrile): −115 ppm. Elem. Anal. Calc. for C$_{14}$H$_7$N$_3$O$_5$ClF: C 47.81, H 2.00, N 11.95, F 5.40, Cl 10.08. Found: C 47.66, H 1.70, N 11.82, F 5.84, Cl 10.16. m.p.=171.9-173.6° C.

j. (3-Fluoro-pyridin-2-yl)-methylamine

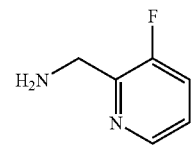

(3-Fluoro-pyridin-2-yl)-methylamine dihydrochloride (1.313 g, 6.60 mmol) (WO 00/75134 A1; *Chem. Pharm. Bull.* 33:565, 1985) was partitioned between ether (6 mL) and 2.5 M NaOH (5 mL; 12.5 mmol). The aqueous layer (pH approx. 8) was extracted with DCM (4×20 mL). The aqueous layer was then brought to pH ~12 with 2.5 M NaOH and extracted with DCM (2×20 mL), and the DCM and ether layers were combined, dried (2×Na$_2$SO$_4$), and concentrated under rotary evaporation at <30° C. to provide the free base of the title compound as a clear dark brown oil (780 mg, 94%). ¹H-NMR (300 MHz, CDCl₃) δ 8.38 (dt, 1H), 7.39-7.32 (m, 1H), 7.24-7.17 (m, 1H), 4.06 (d, 2H), 1.83 (br s, 2H).

k. 2-(6-Chloro-3-cyano-5-fluoro-1-oxy-pyridin-2-yl)-N-(3-fluoro-pyridin-2-ylmethyl)-acetamide

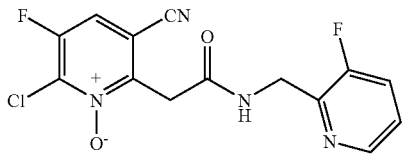

A homogeneous solution of (3-fluoro-pyridin-2-yl)-methylamine (698 mg, 5.53 mmol), as prepared in the previous step, in DCM (35 mL) and CH₃CN (5 mL) was added to a mixture of (6-chloro-3-cyano-5-fluoro-1-oxy-pyridin-2-yl)-acetic acid 4-nitro-phenyl ester (1.801 g, 5.12 mmol), as prepared in Example 1i, in CHCl₃ (10 mL) at rt under air. The flask was then capped, and the mixture was stirred at rt for 10 h, at which point it became a translucent amber solution. [NMR indicated 85% conversion to the title compound, with no remaining (3-fluoro-pyridin-2-yl)-methylamine.] After 10 h reaction, additional (3-fluoro-pyridin-2-yl)-methylamine (68 mg, 0.53 mmol) was added, the reaction stirred an additional 12 h, and was then concentrated by rotary evaporation to a translucent amber solution (~15 mL) suitable for direct loading onto a silica flash column pre-equilibrated with EtOAc. Elution with EtOAc afforded the title compound as an off-white solid (1.29 g, 74%). ¹H-NMR (300 MHz, CDCl₃) δ 8.36 (dt, 1H), 7.55 (br s, 1H), 7.44-7.36 (m, 1H), 7.41 (d, 1H), 7.30-7.23 (m, 1H), 4.66 (dd, 2H), 4.20 (s, 2H).

l. 2-[3-Cyano-6-(2,2-difluoro-2-pyridin-2-yl-ethylamino)-5-fluoro-1-oxy-pyridin-2-yl]-N-(3-fluoro-pyridin-2-ylmethyl)-acetamide

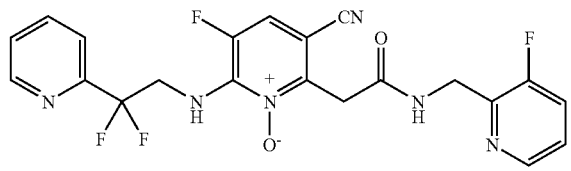

A mixture of 2-(6-chloro-3-cyano-5-fluoro-1-oxy-pyridin-2-yl)-N-(3-fluoro-pyridin-2-ylmethyl)-acetamide (1.156 g, 3.42 mmol), as prepared in the previous step, 2,2-difluoro-2-pyridin-2-yl-ethylamine (651 mg, 4.12 mmol) (*J. Med. Chem.* 46:461, 2003; *Chem. Pharm. Bull.* 48:982, 2000), DIPEA (622 μL, 3.76 mmol), and DMSO-d6 (2.8 mL) was stirred under air at 100° C. for 2 h. At this time, the NMR of the crude reaction showed 95% conversion. The crude reaction was then loaded onto a silica flash column (600 mL dry silica gel) pre-equilibrated with 4:1 EtOAc/acetone, and eluted with 4:1→3:1 EtOAc/acetone to yield the title compound as a beige solid (935 mg, 59%). ¹H-NMR (300 MHz, CDCl₃) δ 8.65 (m, 1H), 8.31 (dt, 1H), 7.99 (m, 2H), 7.83 (td, 1H), 7.67 (m, 1H), 7.42 (m, 1H), 7.36 (m, 1H), 7.31-7.20 (m, 2H), 4.63 (dd, 2H), 4.55 (dt, 2H), 4.15 (s, 2H).

m. 2-[3-Cyano-6-(2,2-difluoro-2-pyridin-2-yl-ethylamino)-5-fluoro-1-oxy-pyridin-2-yl]-N-(3-fluoro-pyridin-2-ylmethyl)-acetamide dihydrochloride

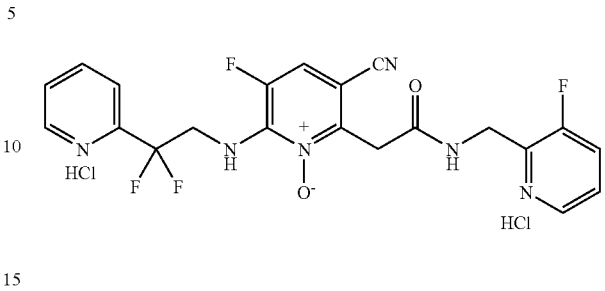

Procedure A

2-[3-Cyano-6-(2,2-difluoro-2-pyridin-2-yl-ethylamino)-5-fluoro-1-oxy-pyridin-2-yl]-N-(3-fluoro-pyridin-2-ylmethyl)-acetamide (920 mg, 2.00 mmol), as prepared in the previous step, was dissolved in dry CH₃CN (42 mL) with gentle heating. To this warm homogeneous solution was added in one portion under air with swirling a solution of 0.202 M HCl/CH₃CN (21 mL; 4.24 mmol HCl). (The 0.202 M HCl/CH₃CN solution was formed by briefly bubbling dry HCl gas into a tared graduated cylinder containing dry CH₃CN to 47.7 mL final volume.) The homogeneous solution was capped and allowed to sit overnight at rt, with crystals beginning to form within 30 min. After crystal formation was complete, the amber supernatant was decanted, the crystals were swirled with dry CH₃CN (20 mL) and the solvent decanted, and the crystals were then scraped from the flask in the presence of CH₃CN (20 mL) and filtered. The crystals were then briefly dried under vacuum, powdered with mortar and pestle, and dried under vacuum overnight to provide, in one crop, the title compound as the monohydrate as a light pink crystalline solid (612.3 mg, 57%). ¹H-NMR (300 MHz, CD₃OD) δ 8.82 (d, 1H), 8.65 (m, 1H), 8.51 (dt, 1H), 8.10-8.00 (m, 2H), 7.80 (d, 1H), 7.77 (td, 1H), 7.60 (m, 1H), 4.89 (d, 2H), 4.57 (dt, 2H), 4.15 (s, 2H). LC/MS (ESI): calcd mass free base 460.1, found 461.1 (MH)⁺. Elem. Anal. Calc. for free base.2.04 HCl.1.07 H₂O.0.045 CH₃CN: C, 45.57; H, 3.68; N, 15.23; Cl, 13.02. Found: C, 45.47; H, 3.40; N, 15.1; Cl, 13.02. Karl Fischer % water: 3.46.

Procedure B

A suspension of 400 mg of 2-[3-cyano-6-(2,2-difluoro-2-pyridin-2-yl-ethylamino)-5-fluoro-1-oxy-pyridin-2-yl]-N-(3-fluoro-pyridin-2-ylmethyl)-acetamide in 8.0 mL of acetonitrile was heated to 75° C. using an oil bath with stirring. The solid began dissolving at 72° C. and completely dissolved to form a yellow solution at 75° C. The mixture was allowed to cool slowly in the oil bath to approx. 53° C. A solution of 0.2 mL of hydrochloric acid (37%, ACS reagent, ca. 9.8 M) in 0.3 mL of acetonitrile was added dropwise to the mixture with stirring. Precipitate formed almost immediately. The mixture was allowed to cool to room temperature while it was stirred vigorously. The mixture was allowed to cool to room temperature. The mixture was then placed into the freezer overnight. The resulting slurry was filtered and rinsed with a minimal amount of chilled acetonitrile. The solid obtained was ground with a mortar and pestle and dried in vacuo at 25° C. overnight to yield a white crystalline solid (0.45 g, 94%): ¹H-NMR (400 MHz, CD₃OD) δ 8.78 (dd, J=1.14, 5.77 Hz, 1H), 8.60 (dm, J=4.18 Hz, 1H), 8.46 (dt, J=1.16, 8.70 Hz, 1H), 8.02 (m, 1H), 7.97 (dt, J=1.68, 7.81 Hz, 1H), 7.77 (d, J=11.98 Hz, 1H), 7.71 (td, J=7.95, 0.99 Hz, 1H), 7.53 (dd, J=4.91, 7.59 Hz, 1H)., 4.86 (d, J=0.94 Hz, 2H), 4.54 (t, J=13.90 Hz, 2H), 4.12 (s, 2H). LC/MS (APCI): calcd mass free base 460.1, found 460.9 (MH)$^+$. Elem. Anal. Calc. for free base.2HCl.H$_2$O: C, 45.75; H, 3.66; N, 15.24; Cl, 12.86; H$_2$O, 3.27. Found: C, 45.63; H, 3.34; N, 15.11; Cl, 13.06. Karl Fischer % water: 3.15.

n. 2-[3-Cyano-6-(2,2-difluoro-2-pyridin-2-yl-ethylamino)-5-fluoro-1-oxy-pyridin-2-yl]-N-(3-fluoropyridin-2-ylmethyl)-acetamide monohydrobromide

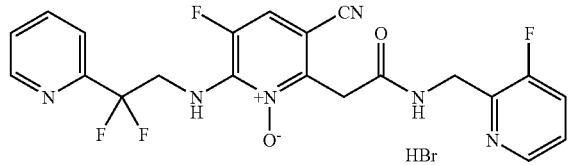

A suspension of 2.0 g of 2-[3-cyano-6-(2,2-difluoro-2-pyridin-2-yl-ethylamino)-5-fluoro-1-oxy-pyridin-2-yl]-N-(3-fluoro-pyridin-2-ylmethyl)-acetamide in 40 mL of acetonitrile was heated to 75° C. using an oil bath with stirring. The solid began at 72° C. and completely dissolved to form a yellow solution at 75° C. The mixture was allowed to cool slowly in the oil bath to approx. 53° C. A solution of 0.59 mL of hydrobromic acid (48%, ACS reagent, ca. 8.84 M) in 2 mL of acetonitrile was added dropwise to the mixture with stirring. Precipitate was formed almost immediately. The mixture was allowed to cool to room temperature while it was stirred vigorously. The mixture was then placed into the freezer overnight. The resulting mixture was filtered and rinsed with a minimal amount of chilled acetonitrile. The solid obtained was ground with a mortar and pestle and dried in vacuo at 78° C. for 2 hrs.to yield a pale yellow crystalline solid (2.11 g, 86%): $^1$H-NMR (400 MHz, CD$_3$OD) δ 8.76 (dd, J=1.12, 5.71 Hz, 1H), 8.60 (dm, J=4.73 Hz, 1H), 8.42 (dt, J=1.11, 8.72 Hz, 1H), 8.00 (m, 1H), 7.96 (dt, J=1.64, 7.79 Hz, 1H), 7.77 (d, J=11.97 Hz, 1H), 7.70 (td, J=7.93, 0.87 Hz, 1H), 7.52 (dd, J=4.98, 7.45 Hz, 1H)., 4.85 (s, 2H), 4.54 (t, J=14.05 Hz, 2H), 4.12 (s, 2H). LC/MS (APCI): calcd mass free base 460.1, found 461.0 (MH)$^+$. Elem. Anal. Calc. for free base.1.2HBr.0.6H$_2$O: C, 44.38; H, 3.26; N, 14.79; Br, 16.87; H$_2$O, 1.90. Found: C, 44.48; H, 3.08; N, 14.71; Br, 17.21. Karl Fischer % water: 1.99.

EXAMPLE 2

Tablet Preparation

Tablets containing 25.0, 50.0, and 100.0 mg, respectively, of the active compound, 2-[3-cyano-6-(2,2-difluoro-2-pyridin-2-yl-ethylamino)-5-fluoro-1-oxy-pyridin-2-yl]-N-(3-fluoro-pyridin-2-ylmethyl)-acetamide dihydrochloride, are prepared as illustrated below:

Tablet for Doses Containing from 25-100 MG of the Active Compound

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 3

Intravenous Solution Preparation

An intravenous dosage form of the above-indicated active compound of Example 1 is prepared as follows:

| Active Compound | 0.5–10.0 mg |
|---|---|
| Sodium Citrate | 5–50 mg |
| Citric Acid | 1–15 mg |
| Sodium Chloride | 1–8 mg |
| Water for Injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

EXAMPLE 4

In Vitro Inhibition of Purified Enzyme

Reagents: All buffer salts were obtained from Sigma Chemical Company (St. Louis, Mo.), and were of the highest purity available.

Human α-thrombin, was obtained from Enzyme Research Laboratories (South Bend, Ind.).

Kinetic Analysis by Chromogenic Substrates

Compounds were assessed for their inhibitory activity toward Thrombin by kinetic analysis using para-nitroaniline chromogenic substrates monitored at 405 nm. The assay buffer employed was 50 mM HEPES, pH 7.5, 200 mM NaCl, and fresh 0.05% n-octyl β-d-glucopyranoside. DMSO was present at a final concentration of 4%, derived from the substrate and inhibitory compound stock solutions. In a 96-well low binding polystyrene plate, 280 uL of substrate in assay buffer was preincubated at 37° C. for 15 min with 10 μL test compound in DMSO to obtain final test compound concentrations that bracketed the Ki. Reactions were initiated by addition of 10 μL protease, and increase in absorbance due to proteolytic cleavage of substrate was kinetically monitored at 37° C., 405 nm with a Molecular Devices Spectramax 340 platereader. Initial velocities were determined by analysis of the initial linear portion of the reactions. Plots of $v_o/v_i$ vs. inhibitor concentration, where $v_o$=velocity without inhibitor, and $v_i$=inhibited velocity, were fit to a linear regression line, and the IC$_{50}$ was determined from the reciprocal of the slope. Ki was calculated from the IC$_{50}$ using the Ki factor specific for the assay as: Ki=IC$_{50}$×Ki factor, or Ki=IC$_{50}$×(1/(1+[S]/Km)), where S is the substrate concentration in the assay, and Km is the Michaelis constant for the substrate (Cheng Y and Prusoff W H (1973) *Biochem Pharmacol* 22: 3099-3108).

The Thrombin assay incorporated substrate SucAAPR pNA (Bachem L-1720, [S]=100 uM final, Km=320 μM, Ki factor=0.76). Substrate in DMSO (10.7 mM) was diluted in assay buffer 100-fold for 100 μM final. Human α-thrombin (Enzyme Research Laboratories HT1002a) was diluted 1500-fold in assay buffer for a final assay concentration of 1.1 nM.

The results indicate that the compound of Example 1 has Ki values for human thrombin of between 9.8 and 11 nM.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound of Formula I

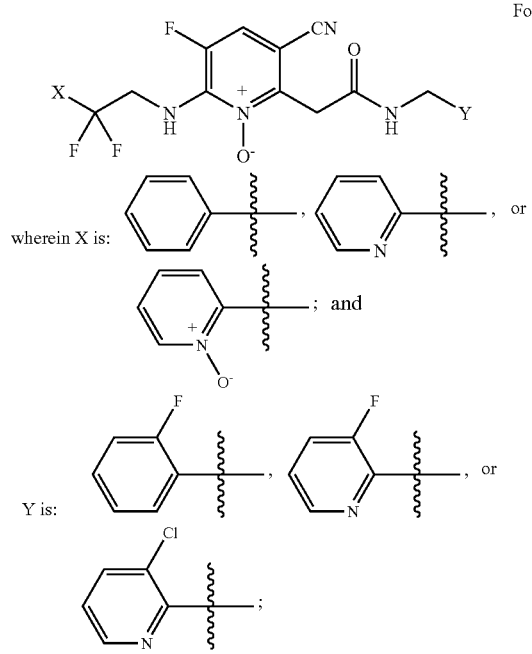

or a pharmaceutically acceptable salt thereof.

2. A composition, comprising a compound of claim 1 and a pharmaceutically-acceptable carrier.

3. A composition according to claim 2, wherein said compound is present in an amount between about 0.1 and about 500 mg.

4. A process of synthesizing a pyridine N-oxide of

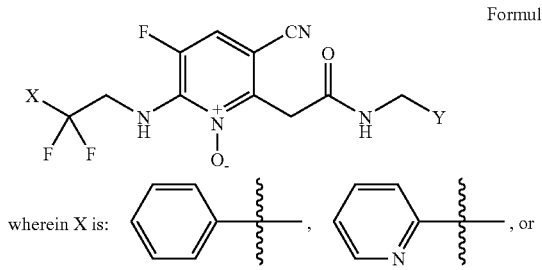

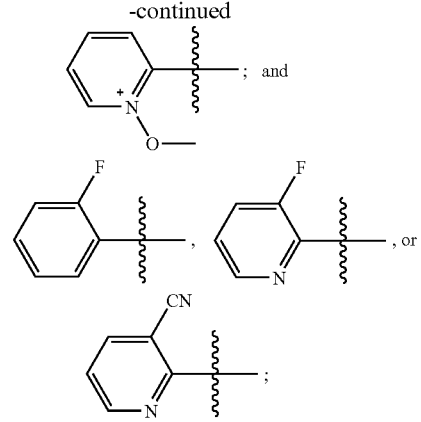

comprising: reacting a pyridine with sodium percarbonate and triflic anhydride, in amounts of from about one half equivalent each to about ten equivalents each, at temperature of from about −50° C. to about 40° C. in a solvent.

5. The process of claim 4 wherein the temperature is between −10° C. and 10° C.

6. A process of synthesizing a pyridine N-oxide of

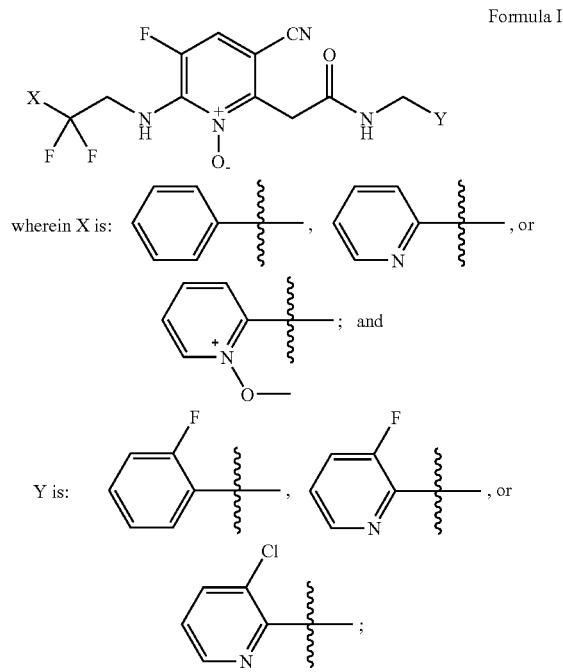

comprising:
reacting a pyridine with urea hydrogen peroxide and triflic anhydride, in amounts of from about one half equivalent each to about ten equivalents each, at temperature of from about −50° C. to about 40° C. in a solvent.

7. The process of claim 6 wherein the temperature is between −10° C. and 10° C.

8. A compound which is: 2-[3-Cyano-6-(2,2-difluoro-2-pyridin-2-yl-ethylamino)-5-fluoro-1-oxy-pyridin-2-yl]-N-(3-fluoro-pyridin-2-ylmethyl)-acetamide and pharmaceutically acceptable salts thereof.

* * * * *